(12) United States Patent
Ramji et al.

(10) Patent No.: US 11,471,388 B2
(45) Date of Patent: Oct. 18, 2022

(54) ORAL CARE COMPOSITIONS COMPRISING MEDIUM LENGTH POLYPHOSPHATES

(71) Applicant: The Procter & Gamble Company, Cincinnati, OH (US)

(72) Inventors: Niranjan Ramji, Mason, OH (US); Michael David Curtis, Mason, OH (US); Samuel James St. John, Cincinnati, OH (US); Kathleen Pearson, Batavia, OH (US); Lina Aurora Witte, Monroe, OH (US); Andrea Noland, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/676,478

(22) Filed: Nov. 7, 2019

(65) Prior Publication Data

US 2020/0138683 A1 May 7, 2020

Related U.S. Application Data

(60) Provisional application No. 62/756,666, filed on Nov. 7, 2018.

(51) Int. Cl.
*A61K 8/24* (2006.01)
*A61K 8/21* (2006.01)
*A61K 8/81* (2006.01)
*A61Q 11/00* (2006.01)

(52) U.S. Cl.
CPC ............... *A61K 8/24* (2013.01); *A61K 8/21* (2013.01); *A61K 8/8176* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 3,577,521 A * | 5/1971 | Karlheinz et al. | A61K 8/22 424/57 |
| 4,340,583 A * | 7/1982 | Wason | A61K 8/25 424/57 |
| 4,822,599 A | 4/1989 | Mitra | |
| 5,094,844 A | 3/1992 | Gaffar et al. | |
| 5,538,714 A * | 7/1996 | Pink | A61K 8/25 424/49 |
| 6,190,644 B1 | 2/2001 | McClanahan et al. | |
| 6,555,094 B1 | 4/2003 | Glandorf et al. | |
| 6,685,920 B2 | 2/2004 | Baig et al. | |
| 6,696,045 B2 | 2/2004 | Yue et al. | |
| 6,713,049 B1 | 3/2004 | White et al. | |
| 6,821,507 B2 | 11/2004 | Glandorf et al. | |
| 8,071,076 B2 | 12/2011 | Nathoo | |
| 9,801,795 B2 | 10/2017 | Nesta et al. | |
| 10,123,953 B2 | 11/2018 | Ramji et al. | |
| 10,258,549 B2 | 4/2019 | Baig et al. | |
| 2003/0003061 A1 * | 1/2003 | Yue | A61K 8/25 424/57 |
| 2003/0003062 A1 | 1/2003 | McLaughlin | |
| 2006/0134020 A1 * | 6/2006 | Robinson | A61K 8/21 424/52 |
| 2006/0171907 A1 * | 8/2006 | Scott | A61K 8/24 424/53 |
| 2013/0022554 A1 | 1/2013 | Engel et al. | |
| 2017/0281490 A1 | 10/2017 | Ramji et al. | |
| 2017/0367948 A1 * | 12/2017 | Thomson | A61K 8/365 |
| 2018/0214357 A1 * | 8/2018 | Takahashi | A61K 8/365 |

FOREIGN PATENT DOCUMENTS

| | | |
|---|---|---|
| JP | S63141920 A | 6/1988 |
| JP | 2001247438 A | 9/2001 |
| JP | 2005170867 A | 6/2005 |
| WO | WO9822079 A1 | 5/1998 |
| WO | 1999012517 A1 | 3/1999 |
| WO | 2001034107 A1 | 5/2001 |
| WO | 2002030382 A1 | 4/2002 |

OTHER PUBLICATIONS

ICL Performance Products (https://www.preparedfoods.com/articles/106069-enhanced-beverage-shelflife, 2008). (Year: 2008).*
PCT Search Report and Written Opinion for PCT/US2019/060207 dated May 25, 2020.

* cited by examiner

*Primary Examiner* — Walter E Webb
(74) *Attorney, Agent, or Firm* — Elizabeth A. Conklin

(57) ABSTRACT

An oral care composition with one or more polyphosphates with about 20 wt % or more of water at a pH of about 5 or less. A dentifrice composition with one or more polyphosphates with about 20 wt % or more of water at a pH of about 5 or less. A mouth rinse composition with one or more polyphosphates with about 20 wt % or more of water at a pH of about 5 or less.

14 Claims, No Drawings

ORAL CARE COMPOSITIONS COMPRISING MEDIUM LENGTH POLYPHOSPHATES

FIELD OF THE INVENTION

The present invention relates to compositions comprising medium length linear polyphosphates and compositions further comprising shorter length linear polyphosphates.

BACKGROUND OF THE INVENTION

Polyphosphates are a class of materials obtained by the dehydration and condensation of orthophosphate to yield linear and cyclic polyphosphates of varying chain lengths. Polyphosphate compounds are commonly used in oral care compositions as anti-tartar agents and for stain prevention.

Unfortunately, linear polyphosphates undergo acid catalyzed hydrolysis reactions while in compositions with a pH of 6 or less. Thus, many oral care compositions comprising linear polyphosphates are currently formulated at a pH of 7 or higher.

In some cases, linear polyphosphates have been formulated with a water content of less than 20 wt % to mitigate acid catalyzed hydrolysis reactions. Formulating the oral care composition to have a low amount of water can minimize aqueous reactivity. However, these compositions can have poor stain removal performance. In many cases, the amount of abrasive is increased, or oxidizing agents are added to improve stain removal performance. Unfortunately, increased amounts of abrasive can increase the RDA while oxidizing agents can be irritating to the oral cavity.

Accordingly, it would be beneficial to have a composition with an improved stain removal performance without having to increase the amount of abrasive or incorporating oxidizing agents.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

An oral care composition having about 20 wt % or greater, by weight of the oral care composition, of water, a polyphosphate source comprising a first linear polyphosphate with an average chain length of from about 6 to about 21, a pH of about 5 or less, and a ΔE of about 3 or less. The polyphosphate source can also have a second linear polyphosphate with an average chain length of from about 2 to about 6.

A dentifrice composition having about 20% or greater, by weight of the dentifrice composition, of water, a fluoride ion source, a polyphosphate source comprising a first linear polyphosphate with an average chain length of from about 6 to about 21, and a pH of about 5 or less. The polyphosphate source can also have a second linear polyphosphate with an average chain length of from about 2 to about 6.

A mouth rinse composition having about 20% or greater, by weight of the mouth rinse composition, of water, a polyphosphate source comprising a first linear polyphosphate with an average chain length of from about 6 to about 21, and a pH of about 5 or less. The polyphosphate source can also have a second linear polyphosphate with an average chain length of from about 2 to about 6.

DETAILED DESCRIPTION OF THE INVENTION

The present invention is directed to oral care compositions comprising medium length linear polyphosphates and compositions further comprising shorter length linear polyphosphates. As polyphosphate molecules are prone to undergo acid catalyzed hydrolysis reactions, current formulations comprising polyphosphate molecules have a pH of 7 or greater and/or are formulated to have less than 20 wt % of water.

However, as described herein, polyphosphate molecules can remove more stain from teeth at lower pHs. Thus, it would be advantageous to have a composition comprising polyphosphate molecules at a pH of about 5 or less. As described herein, oral care compositions comprising a medium length linear polyphosphate and oral care compositions further comprising a shorter length linear polyphosphate at a pH of about 5 or less can demonstrate increased stain removal.

Additionally, many whitening dentifrice compositions have high levels of abrasive or they incorporate specific highly abrasive abrasives to improve stain removal from tooth surfaces. Unfortunately, this may lead to dentifrice compositions with high RDA values that can lead to abrasion of enamel and dentine. Thus, the present invention is directed to compositions comprising one or more polyphosphate sources, which can alleviate these challenges. Without wishing to being bound by theory, it is believed that when polyphosphate sources are properly formulated they can help to loosen the stains from teeth surfaces so that elevated levels of abrasives or highly abrasive abrasives are not required.

While the specification concludes with claims particularly pointing out and distinctly claiming the invention, it is believed that the present invention will be better understood from the following description.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied.

The term "oral care composition", as used herein, includes a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "dentifrice", as used herein, includes tooth or subgingival-paste, gel, or liquid formulations unless otherwise specified. The dentifrice composition may be a single-phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

The term "mouth rinse", as used herein, includes an aqueous solution unless otherwise specified. The mouth rinse composition in the ordinary course of usage, is not intentionally swallowed for purposes of systemic administration of particular therapeutic agents, but is rather retained in the oral cavity for a time sufficient to contact substantially all of the dental surfaces and/or oral tissues in the oral cavity.

"Active and other ingredients" useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

The term "orally acceptable carrier" comprises one or more compatible solid or liquid excipients or diluents which are suitable for topical oral administration. By "compatible," as used herein, is meant that the components of the composition are capable of being commingled without interaction in a manner which would substantially reduce the composition's stability and/or efficacy. The carriers or excipients of the present invention can include the usual and conventional components of mouthwashes or mouth rinses, as more fully described hereinafter: Mouthwash or mouth rinse carrier materials typically include, but are not limited to one or more of water, alcohol, humectants, surfactants, and acceptance improving agents, such as flavoring, sweetening, coloring and/or cooling agents.

While compositions and methods are described herein in terms of "comprising" various components or steps, the compositions and methods can also "consist essentially of" or "consist of" the various components or steps, unless stated otherwise.

As used herein, the word "or" when used as a connector of two or more elements is meant to include the elements individually and in combination; for example, X or Y, means X or Y or both.

As used herein, the articles "a" and "an" are understood to mean one or more of the material that is claimed or described, for example, "an oral care composition" or "a bleaching agent."

All measurements referred to herein are made at about 23° C. (i.e. room temperature) unless otherwise specified.

Generally, groups of elements are indicated using the numbering scheme indicated in the version of the periodic table of elements published in *Chemical and Engineering News,* 63(5), 27, 1985. In some instances, a group of elements can be indicated using a common name assigned to the group; for example, alkali metals for Group 1 elements, alkaline earth metals for Group 2 elements, and so forth.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein.

The term "about" means that amounts, sizes, formulations, parameters, and other quantities and characteristics are not and need not be exact, but can be approximate and/or larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

The term RDA refers to Relative Dentin Abrasion or Radioactive Dentin Abrasion as defined in FDI-ISO 11609. The term PCR refers to Pellicle Cleaning Ratio as defined in the original paper by Stookey et al. 1982 and later used by Schemehorn et al. 2011 to characterize the relative effectiveness of oral care compositions to remove a laboratory-sourced, human-like, stain from enamel chips. These experimental techniques will be described in greater detail later.

The oral care composition can be in any suitable form, such as a solid, liquid, powder, paste, or combinations thereof. The oral care composition can be dentifrice, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The components of the oral care composition can be incorporated into a film, a strip, a foam, or a fiber-based oral care composition. The oral care composition can include a variety of active and inactive ingredients, such as, for example, but not limited to one or more polyphosphate sources, water, a fluoride source, humectants, surfactants, low levels or no other whitening agents, abrasives, other ingredients, and the like, as well as any combination thereof, as described below.

Polyphosphate Source

The oral care composition can comprise a polyphosphate source. A polyphosphate source can comprise one or more polyphosphate molecules. Polyphosphates are a class of materials obtained by the dehydration and condensation of orthophosphate to yield linear and cyclic polyphosphates of varying chain lengths. Thus, polyphosphate molecules are generally identified with an average number (n) of polyphosphate molecules, as described below. A polyphosphate is generally understood to consist of two or more phosphate molecules arranged primarily in a linear configuration, although some cyclic derivatives may be present.

Preferred polyphosphates are those having an average of two or more phosphate groups so that surface adsorption at effective concentrations produces sufficient non-bound phosphate functions, which enhance the anionic surface charge as well as hydrophilic character of the surfaces. Preferred in this invention are the linear polyphosphates having the formula: $XO(XPO_3)_nX$, wherein X is sodium, potassium, ammonium, or any other alkali metal cations and n averages from about 2 to about 21. Alkali earth metal cations, such as calcium, are not preferred because they tend to form insoluble fluoride salts from aqueous solutions comprising a fluoride ions and alkali earth metal cations. Thus, the oral care compositions disclosed herein can be free of or substantially free of calcium pyrophosphate.

Some examples of suitable polyphosphate molecules include, for example, pyrophosphate (n=2), tripolyphosphate (n=3), tetrapolyphosphate (n=4), sodaphos polyphosphate (n=6), hexaphos polyphosphate (n=13), benephos polyphosphate (n=14), hexametaphosphate (n=21), which is also known as Glass H. Polyphosphates can include those polyphosphate compounds manufactured by FMC Corporation, ICL Performance Products, and/or Astaris.

The oral care composition can comprise from about 0.1% to about 10%, from about 0.5% to about 5%, from about 1 to about 20%, or about 10% or less, by weight of the oral care composition, of the polyphosphate source.

Many polyphosphates are susceptible to hydrolysis in high water formulations with an acidic pH, particularly below pH 6. In many cases, longer-chain polyphosphates, such as Glass H having an average chain length of about 21, were utilized in oral care compositions because such longer-chain polyphosphates, were more resistant to acid catalyzed hydrolysis and were still effective to deposit onto teeth and provide a stain preventive benefit. However, as described herein, oral care compositions with medium length chains can be as effective or more effective at removing stains as oral care compositions comprising longer-chain polyphosphates. Additionally, the oral care composition can comprise an additional polyphosphate compound, which can be as effective or more effective at removing stains as oral care compositions comprising only longer-chain polyphosphates.

The oral care composition can comprise a first linear polyphosphate. The first linear polyphosphate can comprise a medium length linear polyphosphate. The first linear polyphosphate can comprise a polyphosphate with an average number of phosphate molecules (n) of from about 6 to about 21, from about 8 to about 21, from about 6 to about 14, from about 8 to about 14, or from about 8 to about 13. The first linear polyphosphate can comprise sodaphos polyphosphate (n=6), hexaphos polyphosphate (n=13), benephos polyphosphate (n=14), hexametaphosphate (n=21), and/or mixtures thereof. The first linear polyphosphate can comprise hexaphos polyphosphate (n=13), benephos polyphosphate (n=14), and/or mixtures thereof. The first linear polyphosphate can exclude any calcium counter ions.

The polyphosphate source can comprise a second linear polyphosphate. The second linear polyphosphate can comprise a shorter length linear polyphosphate. The second linear polyphosphate can comprise a polyphosphate with an average number of phosphate molecules (n) of from about 2 to about 8, from about 2 to about 6, or from about 3 to about 6. The second linear polyphosphate can comprise pyrophosphate (n=2), tripolyphosphate (n=3), tetrapolyphosphate (n=4), sodaphos polyphosphate (n=6), and/or mixtures thereof. The second linear polyphosphate can exclude any calcium counter ions.

The polyphosphate source can comprise a third, fourth, fifth, or more polyphosphate. The additional polyphosphates can comprise a polyphosphate molecule with an average number of phosphate molecules (n) of from about 2 to about 21, from about 6 to about 21, from about 6 to about 14, or from about 8 to about 13.

The ratio of the first linear polyphosphate to the second polyphosphate can from about 6:1 to about 1:1, from about 4:1 to about 1:1, from about 2:1 to about 1:1, or about 1:1, by weight of the oral care composition.

Water

The oral care composition of the present invention can be anhydrous, a low water formulation, or a high water formulation. In total, the oral care composition can comprise from 0% to about 99%, about 20% or greater, about 30% or greater, or about 50% or greater by weight of the composition, of water. Preferably, the water is USP water.

In a high water dentifrice formulation, the dentifrice composition comprises from about 45% to about 75%, by weight of the composition, of water. The high water dentifrice composition can comprise from about 45% to about 65%, from about 45% to about 55%, or from about 46% to about 54%, by weight of the composition, of water. The water may be added to the high water dentifrice formulation and/or may come into the composition from the inclusion of other ingredients.

In a low water dentifrice formulation, the dentifrice composition comprises from about 10% to about 45%, by weight of the composition, of water. The low water dentifrice composition can comprise from about 10% to about 35%, from about 15% to about 25%, or from about 20% to about 25%, by weight of the composition, of water. The water may be added to the low water dentifrice formulation and/or may come into the composition from the inclusion of other ingredients.

In an anhydrous dentifrice formulation, the dentifrice composition comprises less than about 10%, by weight of the composition, of water. The anhydrous dentifrice composition comprises less than 5%, less than 1%, or 0%, by weight of the composition, of water. The water may be added to the anhydrous formulation and/or may come into the dentifrice composition from the inclusion of other ingredients.

A mouth rinse formulation comprises from about 75% to about 99%, from about 75% to about 95%, or from about 80% to about 95% of water.

The oral care composition can also comprise other orally acceptable carrier materials, such as alcohol, humectants, polymers, surfactants, and acceptance improving agents, such as flavoring, sweetening, coloring and/or cooling agents. Alternatively, the oral care composition can be free of or substantially free of alcohol as an orally acceptable carrier.

Fluoride Source

The oral care composition can comprise a fluoride source. The fluoride source can comprise fluoride containing compounds, such as stannous fluoride, sodium fluoride, potassium fluoride, amine fluoride, sodium monofluorophosphate, zinc fluoride, and mixtures thereof. The fluoride source can comprise sodium monofluorophosphate.

Alternatively, the fluoride source can have a single fluoride source. The single fluoride source can be sodium monofluorophosphate. While not wishing to be bound by theory, free fluoride ions, such as the fluoride ions provided by, for example, sodium fluoride and/or stannous fluoride in aqueous solutions at low pHs, can react with polyphosphate molecules. Thus, sodium monofluorophosphate may be used as the single fluoride source to prevent fluoride-polyphosphate reactivity in the oral care composition. The oral care composition can be free of sodium fluoride, stannous fluoride, or any other source of free fluoride ions in aqueous solutions with a pH of less than about 5 or about 5 or less.

The oral care composition can comprise a fluoride source capable of providing from about 50 ppm to about 3500 ppm, and preferably from about 500 ppm to about 3000 ppm of free fluoride ions. To deliver the desired amount of fluoride ions, the fluoride source may be present in the total dentifrice composition at an amount of from about 0.0025% to about 5%, from about 0.2% to about 1%, from about 0.5% to about 1.5%, or from about 0.3% to about 0.6%, by weight of the oral care composition.

pH

The oral care composition can have an acidic pH because, as described herein, the stain removal benefits of the polyphosphate source is enhanced at a lower pH. The oral care composition can have a pH of about 6 or less, about 5 or less, about 4.5 or less, about 4 or less, from about 2 to about 5, from about 3 to about 5, from about 3 to about 4.5, less than about 5, less than about 4.5, and/or about 4.5. The pH of the oral care composition can be adjusted using one or more pH control agents. The one or more pH control agents can be acidic if the pH of the oral care composition is to be adjusted to a lower pH or the one or more pH control agents can be basic if the pH of the oral care composition is to be adjusted to a higher pH. Compounds capable of modifying the pH of an oral care composition are well known in the art.

Humectants

The oral care composition can comprise a humectant, have low levels of a humectant, or be free of a humectant. Humectants serve to add body or "mouth texture" to an oral care composition or dentifrice as well as preventing the dentifrice from drying out. Suitable humectants include polyethylene glycol (at a variety of different molecular weights), propylene glycol, glycerin (glycerol), erythritol, xylitol, sorbitol, mannitol, lactitol, and hydrogenated starch hydrolyzates, and mixtures thereof. The oral care composition can comprise amount from 0 to about 70%, from about 10% to about 60%, or from about 25% to about 60%, by weight of the oral care composition, of a humectant.

Surfactants

The oral care composition can comprise one or more surfactants. The surfactants can be used to make the compositions more cosmetically acceptable. The surfactant is preferably a detersive material which imparts to the composition detersive and foaming properties. Suitable surfactants are safe and effective amounts of anionic, cationic, nonionic, zwitterionic, amphoteric and betaine surfactants, such as sodium lauryl sulfate, sodium dodecyl benzene sulfonate, alkali metal or ammonium salts of lauroyl sarcosinate, myristoyl sarcosinate, palmitoyl sarcosinate, stearoyl sarcosinate and oleoyl sarcosinate, polyoxyethylene sorbitan monostearate, isostearate and laurate, sodium lauryl sulfoacetate, N-lauroyl sarcosine, the sodium, potassium, and ethanolamine salts of N-lauroyl, N-myristoyl, or N-palmitoyl sarcosine, polyethylene oxide condensates of alkyl phenols, cocoamidopropyl betaine, lauramidopropyl betaine, palmityl betaine and the like. Sodium lauryl sulfate is a preferred surfactant. The oral care composition can comprise from about 0.1% to about 15%, from about 0.3% to about 10%, or from about 0.3% to about 2.5%, by weight of the composition, of the surfactant.

Low Levels of Other Whitening Agents

The oral care composition can comprise low levels or no other whitening agents. Other whitening agents can include bleaching or oxidizing agents, such as peroxides, perborates, percarbonates, peroxyacids, persulfates, metal chlorites, and mixtures thereof. Suitable peroxide compounds include hydrogen peroxide, urea peroxide, calcium peroxide, and mixtures thereof. Other suitable whitening agents include potassium, ammonium, Sodium and lithium persulfates and perborate mono- and tetrahydrates, and sodium pyrophosphate peroxyhydrate. The oral care composition can be free of or substantially free of other whitening agents. Other whitening agents, such as peroxide, can be irritating to the oral cavity during use of oral care compositions comprising other whitening agents. The present invention provides an alternative strategy to remove stains, namely a lower pH and a polyphosphate source that can replace other whitening agents.

The oral care composition can comprise from 0 to about 1%, from 0 to about 0.1%, less than about 2%, less than about 1%, less than about 0.1%, or less than about 0.01%, by weight of the composition, of the other whitening agents.

Abrasives

The oral care compositions can comprise one or more abrasives. Abrasives can be added to dentifrice formulations to help remove surface stains from teeth. However, elevated levels of abrasives can raise the RDA ratings to levels that can lead to dental abrasion or loss of dentin. Polyphosphates can help loosen surface stains so that a lower amount of abrasive can be used. Increasing the effectiveness of the polyphosphate source can lead to whitening benefits without higher levels of abrasives. Thus, the oral care composition will have a lower RDA rating, but will not compromise on its whitening or cleaning effect (PCR value). Alternatively, the oral care composition can comprise a lower level of abrasives, such as for example, from about 5% to 25%, from about 10% to about 20%, less than about 20%, less than about 15%, or from about 10% to about 15%, by weight of the oral care composition, of one or more abrasives without a sacrifice of the PCR value.

Some suitable abrasives include, for example, precipitated calcium carbonate (PCC), ground calcium carbonate (GCC), chalk, bentonite, dicalcium phosphate or its dihydrate forms, silica gel (by itself, and of any structure), precipitated silica, amorphous precipitated silica (by itself, and of any structure as well), perlite, titanium dioxide, dicalcium phosphate, calcium pyrophosphate, alumina, hydrated alumina, calcined alumina, aluminum silicate, insoluble sodium metaphosphate, insoluble potassium metaphosphate, insoluble magnesium carbonate, zirconium silicate, particulate thermosetting resins and other suitable abrasive materials. Such materials can be introduced into the oral care compositions to tailor the polishing characteristics of the target formulation.

Thickening Agents

The oral care composition can comprise thickening agents. Thickening agents can be useful in the dentifrice compositions to provide a gelatinous structure that stabilizes the toothpaste against phase separation. Suitable thickening agents include polysaccharides and silica thickeners. Some non-limiting examples of polysaccharides include starch; glycerite of starch; gums such as gum karaya (sterculia gum), gum tragacanth, gum arabic, gum ghatti, gum acacia, xanthan gum, guar gum and cellulose gum; magnesium aluminum silicate (Veegum); carrageenan; sodium alginate; agar-agar; pectin; gelatin; cellulose compounds such as cellulose, carboxymethyl cellulose, hydroxyethyl cellulose, hydroxypropyl cellulose, hydroxymethyl cellulose, hydroxymethyl carboxypropyl cellulose, methyl cellulose, ethyl cellulose, and sulfated cellulose; natural and synthetic clays such as hectorite clays; and mixtures thereof.

The thickening agent can comprise polysaccharides. Polysaccharides that are suitable for use herein include carageenans, gellan gum, locust bean gum, xanthan gum, carbomers, poloxamers, modified cellulose, and mixtures thereof. Carageenan is a polysaccharide derived from seaweed. There are several types of carageenan that may be distinguished by their seaweed source and/or by their degree of and position of sulfation. The thickening agent can comprise kappa carageenans, modified kappa carageenans, iota carageenans, modified iota carageenans, lambda carrageenan, and mixtures thereof. Carageenans suitable for use herein include those commercially available from the FMC Company under the series designation "Viscarin," including but not limited to Viscarin TP 329, Viscarin TP 388, and Viscarin TP 389.

The thickening agent can comprise inorganic thickening agents. Some non-limiting examples of suitable inorganic thickening agents include colloidal magnesium aluminum silicate, silica thickeners. Useful silica thickeners include, for example, include, as a non-limiting example, an amorphous precipitated silica such as ZEODENT® 165 silica. Other non-limiting silica thickeners include ZEODENT® 153, 163, and 167, and ZEOFREE® 177 and 265 silica products, all available from Evonik Corporation, and AEROSIL® fumed silicas.

The oral care composition can comprise from 0% to about 15%, from 0.1% to about 10%, from about 0.2% to about 5%, or from about 0.5% to about 2% of one or more thickening agents.

Polymer

The oral care composition can comprise less than about 5%, less than about 3%, less than about 1%, from about 0.1% to about 1%, from about 0.3% to about 3%, or from about 0.5% to about 5%, by weight of the oral care compositions of one or more polymers. The polymer can be a polyethylene glycol (PEG), a polyvinylpyrrolidone (PVP), or a copolymer of maleic anhydride and methyl vinyl ether of various weight percentages of the oral care compositions as well as various ranges of average molecular ranges.

Other Ingredients

The oral care composition can comprise a variety of other ingredients. Flavoring agents also can be added to the oral care compositions. Suitable flavoring agents include, but are not limited to, oil of wintergreen, oil of peppermint, oil of spearmint, oil of *sassafras*, and oil of clove, cinnamon, anethole, menthol, thymol, eugenol, eucalyptol, lemon, orange and other such flavor compounds to add fruit notes, spice notes, etc. These flavoring agents generally comprise mixtures of aldehydes, ketones, esters, phenols, acids, and aliphatic, aromatic and other alcohols.

Sweeteners can be added to the oral care composition to impart a pleasing taste to the product. Suitable sweeteners include saccharin (as sodium, potassium or calcium saccharin), cyclamate (as a sodium, potassium or calcium salt), acesulfame-K, thaumatin, neohesperidin dihydrochalcone, ammoniated glycyrrhizin, dextrose, levulose, sucrose, mannose, sucralose, *stevia*, and glucose.

Colorants can be added to improve the aesthetic appearance of the product. Suitable colorants include without limitation those colorants approved by appropriate regulatory bodies such as the FDA and those listed in the European Food and Pharmaceutical Directives and include pigments, such as $TiO_2$, and colors such as FD&C and D&C dyes.

Preservatives also can be added to the oral care compositions to prevent bacterial growth. Suitable preservatives approved for use in oral compositions such as methylparaben, propylparaben, benzoic acid, and sodium benzoate can be added in safe and effective amounts.

Other ingredients can be used in the oral care composition, such as desensitizing agents, healing agents, other caries preventative agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, and the like.

Gel Network

The oral care composition can comprise a dispersed gel network phase comprising a fatty amphiphile. As used herein, the term "gel network" refers to a lamellar or vesicular solid crystalline phase which comprises at least one fatty amphiphile as specified below, at least one secondary surfactant as specified below, and a solvent as specified below. The lamellar or vesicular phase comprises bi-layers made up of a first layer comprising the fatty amphiphile and the secondary surfactant and alternating with a second layer comprising the solvent. For the lamellar crystalline phase to form, the fatty amphiphile and secondary surfactant must be dispersed within the solvent. The term "solid crystalline", as used herein, refers to the structure of the lamellar or vesicular phase which forms at a temperature below the chain melt temperature of the layer in the gel network comprising the one or more fatty amphiphiles.

An oral care composition comprising a gel network may be prepared by heating the fatty amphiphile, the secondary surfactant, and solvent to a level in the range of about 50° C. to about 90° C. and mixing. This mixture is cooled to a level in the range of about 20° C. to about 35° C. by, for example, passing the mixture through a heat exchanger. As a result of this cooling step, the fatty amphiphile and the secondary surfactant crystallize to form a solid crystalline gel network. The oral carriers can be added at any time during this process.

Alternative methods of preparing the gel network component include sonication and/or milling of the fatty amphiphile, the secondary surfactant, and solvent, while these components are heated, to reduce the particle size of the melted fatty amphiphile phase. This results in an increase in surface area of the fatty amphiphile phase, which allows the secondary surfactant and the solvent to swell the fatty amphiphile phase. Another suitable variation in preparing the gel network includes heating and mixing the fatty amphiphile and the secondary surfactant first, and then adding that mixture to the solvent.

The weight ratio of the fatty amphiphile to the surfactant in the gel network component can be greater than about 1:5, from about 1:3 to about 100:1, greater than about 1:1 to about 20:1, and/or greater than about 2:1 to about 10:1.

As used herein, "fatty amphiphile" refers to a compound having a hydrophobic tail group of $R_1$ as defined below and a hydrophilic head group which does not make the compound water soluble (immiscible), wherein the compound also has a net neutral charge at the pH of the oral care composition. Suitable fatty amphiphiles of the present invention also have a hydrophilic head group which does not make the compound water soluble. The term "water soluble", as used herein, means that the material is soluble in water in the present composition. In general, the material should be soluble at 25° C. at a concentration of 0.1% by weight of the water solvent, preferably at 1%, more preferably at 5%, more preferably at 15% of the oral care composition.

The fatty amphiphile may be characterized as a compound having a Hydrophilic-Lipophilic Balance ("HLB") of 6 or less. The HLB, as used herein, is the standard HLB according to Griffin, J. Soc. Cosm. Chem., vol. 5, 249 (1954).

The gel network component can also comprise a secondary surfactant. As used herein, "surfactant" refers to one or more surfactants which are combined with the fatty amphiphile and oral carrier to form the gel network. The secondary surfactant is typically water soluble or miscible in the solvent or oral carrier. The secondary surfactant may be characterized as a compound having a Hydrophilic-Lipophilic Balance ("HLB") of 6 or more and typically from about 8 to about 30. The HLB, as used herein, is the standard HLB according to Griffin, J. Soc. Cosm. Chem., vol. 5, 249 (1954). Preferably, the surfactant will be reasonably stable and foam throughout a wide pH angle.

The oral care composition can comprise a secondary surfactant as part of gel network phase in an amount from about 0.01% to about 15%, from about 0.1% to about 10%, and/or from about 0.3% to about 5%, by weight of the oral care composition. A diluted solution of surfactant in water can be utilized. The amount of surfactant can be chosen based on the level of foaming desired in the oral care composition and on the irritation caused by the surfactant. Once the level of surfactant is chosen, then the level of fatty amphiphile that forms a gel network is chosen. For example, in oral care compositions with low level of solvents, a greater amount of fatty amphiphile may be required whereas in oral care compositions with high level of solvents or water, a low level of fatty amphiphile may be chosen.

Suitable secondary surfactants include anionic, zwitterionic, amphoteric, cationic, and nonionic surfactants. In one embodiment, anionic surfactants are preferred. The secondary surfactants may be a combination of more than one type of surfactants, such as an anionic and nonionic surfactant.

The gel network component can also comprise solvents, such as water or other suitable solvents. The solvent and the secondary surfactant together contribute to the swelling of the fatty amphiphile. This, in turn, leads to the formation and the stability of the gel network. In addition to forming the gel network, the solvent can help to keep the dentifrice composition from hardening upon exposure to air and provide a moist feel in the mouth. The solvent, as used herein, refers to suitable solvents which can be used in the place of or in combination with water in the formation of the gel network.

Suitable solvents include, for example, water, edible polyhydric alcohols such as glycerin, diglycerin, triglycerin, sorbitol, xylitol, butylene glycol, erythritol, polyethylene glycol, propylene glycol, and combinations thereof. Sorbitol, glycerin, water, and combinations thereof are preferred solvents.

The oral care compositions can comprise solvents as part of the gel network phase in an amount suitable to achieve a gel network when combined with fatty amphiphile and secondary surfactant. The oral care compositions can comprise as part of the gel network phase at least about 0.05% of a solvent, by weight of the oral care composition. The solvent may be present in the oral care composition in amount of from about 0.1% to about 99%, from about 0.5% to about 95%, and from about 1% to about 90%. The solvent is present in the gel network phase and may also be added or present in the oral carrier phase.

Stain Removal Efficacy

The oral care composition can be described by its stain removal efficacy. The oral care composition can be described by the ΔE of a stained bovine tooth. A bovine tooth can be stained with black tea and treated with an oral care composition of the present invention to remove the black tea stain. The ΔE can be calculated using Formula 1. A higher value for ΔE corresponded to more remaining stain after treatment while a lower value for ΔE corresponded to less remaining stain after treatment. The oral care composition can have a ΔE of about 4 or less, about 3.5 or less, about 3 or less, about 2.75 or less, about 2.5 or less, or about 2 or less. The oral care composition can have a corresponding increase in L values following treatment and reduction in b values such that L values were in the range of about −6 to about 0 and b values were in the range of about −3 to about 3 and a values were in the range of about −2 to about 2.

The Relative Dentin Abrasion (RDA) test is typically performed to confirm that a dentifrice composition, e.g., toothpaste, is safe for consumer use, with the upper limit of the test set at 250. Oral care compositions of the present invention can have an RDA at 12.5 wt. % (0.5 wt % of Z165, 7 wt % of Z109, and 5 wt % of Z119) loading of less than about 250, less than about 225, from about 100 to about 225, or from about 120 to about 200. Other appropriate ranges for the RDA are readily apparent from this disclosure.

The oral care compositions can be described by their Pellicle Cleaning Ratio (PCR), which is a measure of the cleaning characteristics of a dentifrice composition with one or more polyphosphates. The oral care compositions can have a PCR at 12.5 wt. % (0.5 wt % of Z165, 7 wt % of Z109, and 5 wt % of Z119) loading of about 70 to about 170, from about 80 to about 155, greater than about 100, greater than about 80, or from about 90 to 160. Other appropriate ranges for the PCR are readily apparent from this disclosure.

The oral care compositions can be described by the ratio of its PCR to its RDA. This ratio can describe the how effective the compositions are at gently cleaning the surface of teeth. The oral care compositions can have a PCR/RDA ratio of about 0.6 or greater, about 0.65 or greater, about 0.68 or greater, or about 0.7 or greater.

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

Experimental Methods

Stain Removal

An in-vitro model was used to evaluate the stain removing ability of the oral care compositions. The model evaluated chemical effects on stain removal and not, for example, the effect of abrasive in dentifrice. First, a stained pellicle is formed by staining bleached bovine teeth (staining cycles 1-3 in the detailed protocol). Next, the stained teeth were subsequently treated with a either a diluted dentifrice slurry or a neat rinse (whitening cycles 1-6 in the detailed protocol). Finally, the stain removal performance was evaluated by comparing an image of the tooth before and after treatment (imaging in the detailed protocol).

A salivary pellicle was grown on bleached bovine teeth (bleached bovine PCR chips 1 cm×1 cm from Therametric Technologies, Inc., Noblesville, Ind.). A set of 4 teeth were affixed in the lid of a 6 well plate such that each set can be immerse into the wells of the plate when closed. Thus, each test had a replicate of 4 teeth, which were averaged. Each tooth was stained by treating the bleached bovine tooth with Lipton® black tea in the presence of expectorated pooled saliva from healthy subjects ("saliva" in the detailed protocol). The tea solution was made by heating 300 mL of water in a beaker to 90-100° C. with a magnetic stirrer. 2 family sized Lipton® black tea bags were added to the heated water. The solution was gently stirred and the heat was turned off. The solution was stirred until its temperature dropped to 60° C. The tea bags were squeezed, and the warm tea was used in the test. The teeth were treated with the tea solution, treated with saliva, and then gently rinsed with tap water. Tea solutions were made fresh before each treatment. This process was replicated 3 times.

The stained bovine teeth were imaged with a digital camera to determine the starting values for L (lightness), a (red/green coordinate), and b (yellow/blue coordinate). The stained teeth were randomized and treated with a selected composition. The stained teeth were treated with dentifrice slurry or the mouth rinse. Dentifrice slurries were made by mixing the selected dentifrice with USP water (1:1 wt/wt) in a cup with lid with a magnetic stirrer for 30 min. Mouth rinses were used as prepared without any dilution. After the treatment with the selected composition, the teeth were washed with water. This process was repeated 6 total times.

The tooth samples were imaged to determine final values for L, a, and b. ΔL, Δa, and Δb values were calculated by subtracting the initial values from the final values for L, a, and b. A value for ΔE was calculated by Formula 1.

$$\Delta E = \sqrt{(\Delta L)^2 + (\Delta a)^2 + (\Delta b)^2}$$ Formula 1. ΔE calculation A detailed protocol for bovine tooth stain removal is provided below.

Teeth Staining Protocol

| Steps | Stage |
|---|---|
| 1. Red sticky wax and superglue were used to attach teeth to inside top cover of 6 well plates | Incubation |
| 2. Teeth were incubated at 37° C. while shaking overnight in 10 mL of saliva | |
| 3. Teeth were shaken for 15 min (~140 rpm) at room temperature (23° C.) with 10 mL of Lipton ® black tea (originally added at 45° C.-60° C.) | Stain Cycle 1-3 |
| 4. Teeth were incubated for 20 min with gentle shaking (~100 rpm) with 10 mL of saliva at 37° C. | |
| 5. Steps 3 and 4 were repeated twice. | |
| 6. The stained teeth were set out to dry (1 hr), pried off plates, imaged, and then randomized. | Imaging |
| 7. Red sticky wax and superglue were used to attach teeth to inside top cover of well plates | Incubation |
| 9. Teeth were incubated at 37° C. while shaking overnight in 10 mL of saliva | |

Teeth Whitening Protocol

| Steps | Stage |
|---|---|
| 1. Teeth were shaken (~140 rpm) for 5 minutes in a mixture of 5 mL dentifrice slurry + 5 mL saliva | Whitening Cycle 1-6 |
| 2. Teeth were incubated while shaking (~100 rpm) in 10 mL of saliva at 37° C. for 20 min | |
| 3. Teeth were removed from incubator and steps 1 and 2 were repeated five more times. | |

| Steps | Stage |
|---|---|
| 4. Teeth were removed from incubator and shaken (~140 rpm) in 10 mL of tap water. | Rinse |
| 5. Teeth were shaken (~140 rpm) in 10 mL of tap water again. | |
| 6. The stained teeth were set out to dry (1 hr), pried off plates, and imaged. Data was analyzed using Formula 1. | Imaging |

Pellicle Cleaning Ratio (PCR)

An in vitro model was used for evaluating the cleaning ability of dentifrices and abrasive powders. First, stained teeth were obtained. Next, the stained teeth were subsequently treated with a dentifrice with an abrasive. Finally, the stain removal performance was evaluated by comparing an image of the tooth before and after treatment.

Stained PCR chips were obtained directly from a supplier (stained PCR chips from Therametric Technologies, Inc., Noblesville, Ind.). Each tooth was stained in accordance with procedures described in Stookey et al. In vitro Removal of Stain with Dentifrices. *J. Dent. Res.* 61 (1982) 1236-1239 and Schemehorn et al. Abrasion, Polishing, and Stain Removal Characteristics of Various Commercial Dentifrices In Vitro. *J. Clinical Dent.* 22 (2011) 11-18, which are herein incorporated by reference.

The stained bovine teeth were imaged with a digital camera to determine the starting values for L (lightness), a (red/green coordinate) and b (yellow/blue coordinate). The stained teeth were randomized and treated with a selected composition.

Dentifrice slurries were prepared by diluting 25 g of the selected dentifrice composition with 40 g of ultrapure distilled water. Dentifrice slurries were compared to a calcium pyrophosphate standard slurry prepared by combining 10 g of calcium pyrophosphate (Model No. A27672, Odontex Solutia, St. Louis, Mo.) with 50 g of a solution containing 0.5 wt % of carboxymethylcellulose (Model No. CA192, Spectrum Chemicals, New Brunswick, N.J.) and 10 wt % of glycerol (Model No. GX0185-6, EMD, Burlington, Mass.).

Samples were secured on each station of a V-8 brushing machine (Sabri Dental Enterprises, Downers Grove, Ill.). The tension of each brush was adjusted to 150 g by loosening or tightening the spring tension screws on the V-8 brushing machine. The brushes used were ADA40 Brushes. The slurry solutions were attached to each brushing station. The V-8 brush machine was set to 800 strokes at 50 strokes/18 sec.

Samples were collected from the brushing machine and rinsed with tap water. Samples were imaged to determine final values for L (lightness), a (red/green coordinate) and b (yellow/blue coordinate). The PCR was determined using Formula 2.

$$PCR = \frac{\Delta L \text{ of specimen after 800 stroke cleaning with selected paste}}{\text{Average } \Delta L \text{ of calcium pyrophosphate standard after 800 stroke cleaning}} \times 100.$$

Formula 2 PCR Calculation

Relative Dentin Abrasion (RDA)

The Relative Dentin Abrasion (RDA) test is typically performed to confirm that a dentifrice composition, e.g., toothpaste, is safe for consumer use, with the upper limit of the test set at 250. The RDA was determined using the industrial published standard as outlined in FDIS-ISO 11609, Annexure, third edition Annex B: Determination of relative dentifrice abrasivity to enamel and dentine by a surface profile method, which is herein incorporated by reference. This method is based on the determination of abraded depth after brushing using profilometry.

TABLE 1

Rinse Formulations with one polyphosphate

| Ingredients | Rinse A (wt %) | Rinse B (wt %) | Control |
|---|---|---|---|
| Water | 93 | 93 | 100 |
| Glycerin | 5 | 5 | 0 |
| Glass H | 2 | 2 | 0 |
| pH[c] | 4[a] | 6[b] | 6.9 |

[a] pH adjusted down to 4 with HCl
[b] pH adjusted up to 6 with NaOH
[c] pH of neat mouth rinse TABLE 1 displays Rinse A (pH=4) and Rinse B (pH=6). Rinse A and Rinse B only had 2 wt % of Glass H (sodium hexametaphosphate) in a glycerin/water chassis and a water control. As shown in TABLE 4, Rinse A performed significantly better ($\Delta E=2.84$) than Rinse B ($\Delta E=3.57$) despite only differing in pH. Thus, polyphosphate compositions with lower pH can remove more stain from teeth.

TABLE 2

Rinse formulations with more than one polyphosphate

| Ingredients | Rinse C | Rinse D | Rinse E |
|---|---|---|---|
| Purified Water | 90.775 | 91.503 | 92.23 |
| Glycerin | 5 | 5 | 5 |
| Sodium Lauryl Sulfate Solution (28% in water) | 0.71 | 0.71 | 0.71 |
| Sodium Hexametaphosphate | 1 | 1 | 1 |
| Pentasodium tripolyphosphate | 1 | 0.5 | 0 |
| Poloxamer 407 | 0.75 | 0.75 | 0.75 |
| Potassium Sorbate | 0.1 | 0.1 | 0.1 |
| Sodium Benzoate | 0.08 | 0.08 | 0.08 |
| Sucralose | 0.015 | 0.015 | 0.015 |
| Sodium Saccharin | 0.015 | 0.015 | 0.015 |
| Flavor | 0.1 | 0.1 | 0.1 |
| Phosphoric acid (85% in water) | 0.772 | 0.42 | 0.055 |
| pH[a] | 5.01 | 5.01 | 4.98 |

[a] pH of neat mouth rinse

TABLE 2 shows rinse formulations C, D, and E which had more than one polyphosphate compound. Rinse C, D, and E had 1 wt % of sodium hexametaphosphate, but differed in the amount of pentasodium tripolyphosphate. The amount of water was adjusted according to the amount of added tripolyphosphate. Rinse C had 1 wt % tripolyphosphate, Rinse D had 0.5 wt % tripolyphosphate, and Rinse E had 0 wt % of tripolyphosphate. The pH of Rinses C, D, and E were essentially 5. As shown in TABLE 4, the sample with the highest amount of the second polyphosphate, Rinse C with 1 wt % of tripolyphosphate had the best removal of stain ($\Delta E=2.19$). Rinse D (0.5 wt % tripolyphosphate) had a $\Delta E$ of 2.41 while Rinse E (0 wt % of tripolyphosphate had a $\Delta E$ of 3.87. Thus, a composition with a first linear polyphosphate and a second linear polyphosphate with a smaller chain length can increase the stain removal of a mouth rinse.

TABLE 3

Rinse formulations with more than one polyphosphate

| Rinse Ingredients | Rinse F (%) | Rinse G (wt %) |
|---|---|---|
| Purified Water | 91.62 | 91.62 |
| Glycerin | 5.00 | 5.00 |
| Sodium Lauryl Sulfate Solution (28% in water) | 0.35 | 0.35 |
| Hexaphos polyphosphate | 1.50 | 1.50 |
| Tetrasodium pyrophosphate | 0.76 | 0.76 |
| Poloxamer 407 | 0.50 | 0.50 |
| Sodium Benzoate | 0.15 | 0.15 |
| Sucralose | 0.02 | 0.02 |
| Sodium Saccharin | 0.02 | 0.02 |
| Flavor | 0.10 | 0.10 |
| pH[a] | 8 | 5 |

[a] pH of neat mouth rinse

TABLE 3 includes Rinse F and Rinse G that had 1.5 wt % of hexaphos polyphosphate and 0.76 wt % of tetrasodium pyrophosphate. However, Rinse F had a pH of 8 while Rinse G had a pH of 5. As shown in TABLE 4, Rinse G removed more stain ($\Delta E=3.67$) than Rinse F ($\Delta E=4.08$). Thus, according to TABLE 4, a mouth rinse with more than one polyphosphate is more effective at removing stain from bovine teeth at a pH of 5 than at a pH of 8.

TABLE 4

Stain removal of rinse formulations

| Rinse | Polyphosphates | pH[a] | $\Delta E$ | Standard Deviation $\Delta E$ |
|---|---|---|---|---|
| Rinse A | 2% Glass H | 4 | 2.84 | 0.27 |
| Rinse B | 2% Glass H | 6 | 3.57 | 0.32 |
| Rinse C | 1% Tripoly/1% Glass H | 5 | 2.19 | 0.19 |
| Rinse D | 0.5% Tripoly/1% Glass H | 5 | 2.41 | 0.27 |
| Rinse E | 1% Glass H | 5 | 3.87 | 0.13 |
| Rinse F | 0.76% Pyro/1.5% Hexaphos | 8 | 4.08 | 0.58 |
| Rinse G | 0.76% Pyro/1.5% Hexaphos | 5 | 3.67 | 0.31 |
| Listerine ® Advanced White | 0.63% Pyro/0.57% Tripolyphoshate | 6.54 | 3.17 | 0.32 |
| Colgate ® Max White One | 1% Pyro/PVP-MA copolymer | 7.82 | 3.87 | 0.13 |
| Tap Water | None | 6.9 | 4.06 | 0.40 |

[a] pH of neat mouth rinse

TABLE 5

Dentifrices with at least one polyphosphate

| Dentifrice Ingredients (wt %) | A | B | C | D | J | K | L |
|---|---|---|---|---|---|---|---|
| pH[a] | 4.5 | 4.5 | 4.5 | 4.5 | 8.9 | 7.7 | 7.7 |
| Polyethylene oxide | — | — | — | — | — | — | 0.25 |
| Flavor | 1.2 | 1.2 | 1.2 | 1.2 | 1.2 | 1.2 | 1.2 |
| Coolant | 0.1 | 0.1 | 0.1 | 0.1 | 0.1 | 0.1 | — |
| Sodium Fluoride | — | — | — | — | — | 0.243 | 0.243 |

TABLE 5-continued

Dentifrices with at least one polyphosphate

| Dentifrice Ingredients (wt %) | A | B | C | D | J | K | L |
|---|---|---|---|---|---|---|---|
| Sodium monofluorophosphate | 0.76 | 0.76 | 0.76 | 0.76 | 0.76 | — | — |
| Sorbitol | 46.99 | 46.99 | 46.99 | 46.99 | 44.09 | 41.307 | — |
| Glycerin USP (99.7% in water) | — | — | — | — | — | — | 54.59 |
| Cocamidopropyl Betaine (30% in water) | 1.5 | 1.5 | 1.5 | 1.5 | 1.5 | — | 1.6 |
| Sodium Polyphosphate FCC | 7 | — | — | — | — | — | 7 |
| Sodaphos polyphosphate | — | — | 7 | — | — | — | — |
| NaOH (50% in water) | — | — | — | — | 5 | 2.18 | — |
| Tribasic Sodium Phosphate Dodecahydrate | — | — | — | — | — | — | 1.1 |
| Benephos polyphosphate | — | 7 | — | — | — | — | — |
| Sodium acid pyrophosphate | — | — | — | — | 7 | 4.17 | — |
| Phosphoric Acid | 0.56 | 1.13 | 2.00 | 0.66 | — | — | — |
| Thickening Silica (Z165) | 0.5 | 0.5 | 0.5 | 0.5 | 0.5 | — | 1 |
| Whitening Silica (Z109) | 7 | 7 | 7 | 7 | 7 | 7 | 12.5 |
| Cleaning Silica (Z119) | 5 | 5 | 5 | 5 | 5 | 15 | 12.5 |
| PEG 300 | — | — | — | — | — | — | 3.5 |
| Sodium Lauryl Sulfate (28% in water) | 5.5 | 5.5 | 5.5 | 5.5 | 5.5 | 7 | 3.4 |
| Sodium Saccharin | 0.45 | 0.45 | 0.45 | 0.45 | 0.45 | 0.45 | 0.4 |
| Sucralose | 0.15 | 0.15 | 0.15 | 0.15 | 0.15 | — | 0.1 |
| Xanthan Gum | 0.65 | 0.65 | 0.65 | 0.65 | 0.55 | — | 0.12 |
| Carboxymethylcellulose | — | — | — | — | — | 1.2 | — |
| Carbomer | — | — | — | — | — | 0.3 | — |
| Carrageenan Mixture Iota Silica | 1.2 | 1.2 | 1.2 | 1.2 | 1.2 | — | 0.5 |
| Water Purified | 21.44 | 20.87 | 20 | 28.34 | 20 | 19.85 | — |
| Total | 100 | 100 | 100 | 100 | 100 | 100 | 100 |

[a]pH of dentifrice slurry (1:3 dentifrice:USP water by weight)

TABLE 6

Dentifrices with at least one polyphosphate

| Dentifrice Ingredients (wt %) | E | F | G | H | I |
|---|---|---|---|---|---|
| pH[a] | 6.6 | 6.9 | 6.5 | 6.5 | 6.8 |
| Sorbitol Solution, USP | 39.24 | 45.04 | 43.44 | 39.24 | 43.44 |
| Water, USP | 20 | 20 | 20 | 20 | 20 |
| Sodium Monofluorophosphate | 0.76 | 0.76 | 0.76 | 0.76 | 0.76 |
| Xanthan Gum | 0.55 | 0.55 | 0.55 | 0.55 | 0.55 |
| Carageenan, Iota silica | 0.65 | 0.65 | 0.65 | 0.65 | 0.65 |
| Sodium Lauryl Sulfate (28% in water) | 3.4 | 3.4 | 3.4 | 3.4 | 3.4 |
| Cocamidopropyl Betaine (30% in water) | 1.6 | 1.6 | 1.6 | 1.6 | 1.6 |
| Flavor | 1.2 | 1.2 | 1.2 | 1.2 | 1.2 |
| Coolant | 0.1 | 0.1 | 0.1 | 0.1 | 0.1 |
| Liquid Sucralose Concentrate | 0.1 | 0.1 | 0.1 | 0.1 | 0.1 |
| Saccharin Sodium, USP | 0.4 | 0.4 | 0.4 | 0.4 | 0.4 |
| Whitening Silica (Z109) | 7 | 7 | 7 | 7 | 7 |
| Cleaning Silica (Z119) | 15 | 15 | 15 | 15 | 15 |
| Glass H | — | — | — | 5.8 | 5.8 |
| Sodium Acid Pyrophosphate | 4.2 | 4.2 | — | 4.2 | — |
| Sodaphos polyphosphate | 5.8 | — | 5.8 | — | — |
| Total | 100 | 100 | 100 | 100 | 100 |

[a]pH of dentifrice slurry (1:3 dentifrice:USP water by weight)

TABLE 7

Dentifrices with at least one polyphosphate

| Dentifrice Ingredients (wt %) | M | N | O | P | Q | R |
|---|---|---|---|---|---|---|
| pH[a] | 4.5 | 4.5 | 4 | 5 | 8.5 | 4 |
| Flavor | 1.2 | 1.2 | 1.2 | 1.2 | 1.2 | 1.2 |
| Coolant | 0.1 | 0.1 | 0.1 | 0.1 | 0.1 | 0.1 |
| Monofluorophosphate | 0.76 | 0.76 | 0.76 | 0.76 | 0.76 | 0.76 |
| Sorbitol | 45.09 | 45.09 | 45.09 | 45.09 | 45.09 | 55.38 |
| Glycerin, USP (99.7% in water) | — | — | — | — | — | — |
| Cocamidopropyl Betaine (30% in water) | 1.5 | 1.5 | 1.5 | 1.5 | 1.5 | 1.5 |
| Glass H | — | 6 | 6 | 6 | 6 | — |
| NaOH (50% in water) | — | — | — | — | 3 | — |
| Benephos Polyphosphate | 6 | — | — | — | — | — |
| Sodium acid pyrophosphate | 2 | 2 | 2 | 2 | 2 | — |
| Phosphoric Acid | 1.06 | 0.47 | 0.74 | 0.07 | 0.74 | 0.71 |
| Thickening Silica (Z165) | 0.5 | 0.5 | 0.5 | 0.5 | 0.5 | 0.5 |

TABLE 7-continued

| Dentifrice Ingredients (wt %) | M | N | O | P | Q | R |
|---|---|---|---|---|---|---|
| Whitening Silica (Z109) | 7 | 7 | 7 | 7 | 7 | 7 |
| Cleaning Silica (Z119) | 5 | 5 | 5 | 5 | 5 | 5 |
| Sodium Lauryl Sulfate (28% in water) | 5.5 | 5.5 | 5.5 | 5.5 | 5.5 | 5.5 |
| Sodium Saccharin, USP | 0.45 | 0.45 | 0.45 | 0.45 | 0.45 | 0.45 |
| Sucralose | 0.15 | 0.15 | 0.15 | 0.15 | 0.15 | 0.15 |
| Xanthan Gum | 0.55 | 0.55 | 0.55 | 0.55 | 0.55 | 0.55 |
| Carrageenan Mix Iota Silica | 1.2 | 1.2 | 1.2 | 1.2 | 1.2 | 1.2 |
| Water Purified | 21.94 | 22.53 | 22.26 | 22.93 | 19.26 | 20 |
| Total | 100 | 100 | 100 | 100 | 100 | 100 |

[a] pH of dentifrice slurry (1:3 dentifrice:USP water by weight)

TABLE 8

Stain removal of Dentifrices A-M*

| Dentifrice | Polyphosphates | pH[c] | ΔE | Standard Deviation ΔE |
|---|---|---|---|---|
| Dentifrice A | 7% Glass H | 4.5 | 2.31 | 0.30 |
| Dentifrice B | 7% Benephos | 4.5 | 1.92 | 0.38 |
| Dentifrice C | 7% Sodaphos | 4.5 | 2.21 | 0.36 |
| Dentifrice D | None | 4.5 | 3.23 | 0.26 |
| Dentifrice E | 4.2% Pyro/5.8% Sodaphos | 6.6 | 2.66 | 0.78 |
| Dentifrice F | 4.2% Pyro | 6.9 | 2.72 | 0.44 |
| Dentifrice G | 5.8% Sodaphos | 6.5 | 2.22 | 0.81 |
| Dentifrice H | 4.2% Pyro/5.8% Glass H | 6.5 | 2.92 | 0.85 |
| Dentifrice I | 5.8% Glass H | 6.8 | 2.32 | 0.76 |
| Dentifrice J | 7% Pyro | 8.9 | 5.98 | 0.47 |
| Dentifrice K | 4.1% Pyro | 7.7 | 5.48 | 0.47 |
| Dentifrice L | 7% Glass H | 7.7 | 4.99 | 0.41 |
| Dentifrice M | 2% Pyro/6% Benephos | 4.5 | 2.30 | 0.28 |
| Colgate ® Optic White Stain Fighter[a] | Pyro/Tripoly | 8.6 | 5.33 | 0.57 |
| Colgate ® Optic White Platinum[b] | Pyro | 7.2 | 3.80 | 0.24 |
| Tap Water | None | 6.9 | 4.06 | 0.47 |

*Table split according to similar formulation chassis
[a] Without peroxide
[b] With peroxide
[c] pH of dentifrice slurry (1:3 dentifrice:USP water by weight)

TABLE 5, TABLE 6, and TABLE 7 show dentifrice formulations A through M. Dentifrice formulations A through M are summarized in TABLE 8 to show the composition of the polyphosphate source, the pH, and ΔE values for Dentifrice A through M compared with a water control, Colgate® Optic White Stain Fighter, and Colgate® Optic White Platinum.

Dentifrice A-D were prepared at pH 4.5 with very similar formulations as in TABLE 5. Dentifrice B had the best stain removal (ΔE=1.92) with 7% benephos polyphosphate (n~14) compared with Dentifrice C (ΔE=2.21, 7% sodaphos polyphosphate) and Dentifrice A (ΔE=2.31, 7% Glass H). Thus, a medium length polyphosphate (benephos polyphosphate) removed stain better than a longer length polyphosphate (Glass H). Importantly, a sample with no polyphosphate, Dentifrice D, performed worse (ΔE=3.23) of the samples with similar chassis despite having a low pH.

Dentifrice E-I were prepared at a pH from 6.5 to 6.9 with comparable formulations as in TABLE 6. The only difference in the formulations of Dentifrice E-I was the relative percentage of sorbitol, which was adjusted based on the selected polyphosphate sources. Dentifrice E-I, all removed stain extremely well with values of ΔE<3 despite having only a slightly acidic pH. Dentifrice E-I all performed better than the Colgate® Optic White Stain Fighter (ΔE=5.33) and Colgate® Optic White Platinum (ΔE=3.80), which contain only pyrophosphate and tripolyphosphate, shorter length polyphosphates.

Dentifrice J-R were prepared with similar formulations as in TABLE 5 and TABLE 7. Dentifrice samples combining pyrophosphate (a shorter length polyphosphate) with a medium length polyphosphate at a pH of less than about 5, such as Dentifrice E and M, removed much more stain than commercial formulations with only pyrophosphate, such as Colgate® Optic White Stain Fighter and Colgate® Optic White Platinum, as in TABLE 8. Importantly, Dentifrice E and M (without peroxide) remove more stain than Colgate® Optic White Platinum that contains peroxide that can be harsh in consumers' mouths. Dentifrice M (ΔE=2.30) significantly outperformed samples with high amounts of a small chain polyphosphate, such as Dentifrice J (ΔE=5.98, 7% of pyrophosphate) and Dentifrice K (ΔE=5.48, 4.1% of pyrophosphate).

Dentifrice A had a ΔE value of 2.31 while Dentifrice L had a ΔE value of 4.99. Dentifrice A (20% water) and Dentifrice L (anhydrous) differed only in the water content and pH, but Dentifrice A was much better at removing stain (ΔE=2.31). Thus, a dentifrice sample with greater than about 20% or about 20% or greater of water performs better than an anhydrous dentifrice sample.

TABLE 9

Measured PCR and RDA values for Selected Dentifrice Formulations

| Dentifrice | Polyphosphates | pH[a] | Measured PCR | δ | Measured RDA | δ | PCR/RDA |
|---|---|---|---|---|---|---|---|
| Dentifrice L | 7% Glass H | 7.7 | 135.0 | 8.1 | 245.0 | 24.6 | 0.55 |
| Dentifrice M | 2% Pyro/6% Benephos | 4.5 | 152.4 | 7.6 | 223.1 | 26.9 | 0.68 |
| Dentifrice N | 2% Pyro/6% Glass H | 4.5 | 135.3 | 10.5 | 197.1 | 24.7 | 0.67 |
| Dentifrice O | 2% Pyro/6% Glass H | 4 | 157.0 | 13.6 | 210.7 | 24.4 | 0.75 |

TABLE 9-continued

Measured PCR and RDA values for Selected Dentifrice Formulations

| Dentifrice | Polyphosphates | pH[a] | Measured PCR | δ | Measured RDA | δ | PCR/RDA |
|---|---|---|---|---|---|---|---|
| Dentifrice P | 2% Pyro/6% Glass H | 5 | 134.8 | 8.7 | 192.0 | 24.5 | 0.70 |
| Dentifrice Q | 2% Pyro/6% Glass H | 8.5 | 110.9 | 6.7 | — | — | — |
| Dentifrice R | None | 4 | 127.0 | 14.7 | 211.2 | 18.1 | 0.60 |

[a]pH of dentifrice slurry (1:3 dentifrice:USP water by weight)

TABLE 9 shows the measured PCR and RDA values for selected dentifrice formulations. As shown in TABLE 9, Dentifrice L has an RDA value of 245.0 while Dentifrice N has an RDA value of 197.1 without a large compromise in PCR values. Dentifrice M, with short/medium polyphosphate molecules, had a higher PCR (i.e. better stain removal) than Dentifrice L with a longer polyphosphate molecule (Glass H) and Dentifrice R with no polyphosphate source. Importantly, Dentifrice M had half of the amount of silica compared with Dentifrice L, but still demonstrated a higher PCR value, which displays the gentle cleaning effect of reducing the amount of silica, but adding a second linear polyphosphate. This modification also decreased the RDA value. Dentifrice N-Q differ only in the pH of the formulation. TABLE 9 shows that dentifrice compositions with lower pH values had higher PCR values.

TABLE 9 also shows the PCR/RDA ratio values for selected dentifrice formulations. As shown in TABLE 9, Dentifrice L (7% Glass H) has a PCR/RDA ratio of 0.551 while Dentifrice R has a PCR/RDA ratio of 0.60. In comparison, Dentifrice M-Q (with at least one medium or shorter chain length polyphosphate molecules) have PCR/RDA ratios of greater than 0.65 indicating a high cleaning benefit relative to the dentin abrasion characteristics of the dentifrice formulations.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising:
   (a) about 20% or greater, by weight of the oral care composition, of water;
   (b) from about 2% to about 12%, by weight of the oral care composition, of the total amount of a polyphosphate source, the polyphosphate source comprising:
      (i) a first linear polyphosphate with an average chain length of from about 6 to about 21;
      (ii) a second linear polyphosphate comprising pyrophosphate;
   (c) sodium monofluorophosphate, and
   (d) a pH of about 5 or less,
   wherein the composition has a ΔE of about 3 or less.

2. The oral care composition of claim 1, wherein the oral care composition has a ratio of the first linear polyphosphate to the second linear polyphosphate is from about 6:1 to about 1:1.

3. The oral care composition of claim 1, wherein the ratio of the first linear polyphosphate to the second linear polyphosphate source is from 4:1 to 1:1.

4. The oral care composition of claim 1, wherein the oral care composition is free of a peroxide, oxidizer, an enzyme, calcium pyrophosphate, an alcohol, or a paraben.

5. The oral care composition of claim 1 further comprising a surfactant.

6. The oral care composition of claim 1 further comprising polyvinylpyrrolidone.

7. The oral care composition of claim 1, wherein the first linear polyphosphate has an average chain length of from about 8 to about 14.

8. The oral care composition of claim 1, wherein the pH is less than 5.

9. An oral care composition comprising:
   (a) about 20% or greater, by weight of the oral care composition, of water;
   (b) from about 2% to about 12%, by weight of the oral care composition, of the total amount of a polyphosphate source, the polyphosphate source comprising:
      (i) a first linear polyphosphate with an average chain length of from about 6 to about 21, and
      (ii) a second linear polyphosphate with an average chain length of from about 2 to about 6; and
   (c) a pH of about 5 or less; and
   (d) sodium monofluorophosphate,
   wherein the oral care composition is free of bleaching agent, the oral care composition is free of calcium, and wherein the composition has a ΔE of about 3 or less.

10. The oral care composition of claim 9, wherein the dentifrice has a ratio of the first linear polyphosphate to the second linear polyphosphate is from about 6:1 to about 1:1.

11. The oral care composition of claim 9, wherein the ratio of the first linear polyphosphate to the second linear polyphosphate source is from 4:1 to 1:1.

12. The oral care composition of claim 9, wherein the first linear polyphosphate has an average chain length of from about 8 to about 14.

13. The oral care composition of claim 9, wherein the second linear polyphosphate comprises pyrophosphate, tripolyphosphate, sodaphos polyphosphate, or combinations thereof.

14. The oral care composition of claim 9, wherein the oral care composition is free of an alcohol.

* * * * *